United States Patent
Bischoff et al.

(10) Patent No.: US 8,859,823 B2
(45) Date of Patent: Oct. 14, 2014

(54) OXO PROCESS AND METHOD FOR PRODUCING SYNTHESIS GAS FROM WASTE OIL

(75) Inventors: Christopher John Bischoff, Bay City, TX (US); Chessley Alan Hungerford, Bay City, TX (US); Mark Henry Sprow, Bay City, TX (US)

(73) Assignee: Oxea Corporation, Dallas, TX (US)

( * ) Notice: Subject to any disclaimer, the term of this patent is extended or adjusted under 35 U.S.C. 154(b) by 0 days.

(21) Appl. No.: 14/116,883

(22) PCT Filed: Jun. 8, 2012

(86) PCT No.: PCT/US2012/041471
§ 371 (c)(1),
(2), (4) Date: Nov. 11, 2013

(87) PCT Pub. No.: WO2013/019312
PCT Pub. Date: Feb. 7, 2013

(65) Prior Publication Data
US 2014/0135534 A1    May 15, 2014

Related U.S. Application Data

(60) Provisional application No. 61/574,259, filed on Jul. 29, 2011.

(51) Int. Cl.
| | |
|---|---|
| *C07C 45/50* | (2006.01) |
| *C07C 27/00* | (2006.01) |
| *C01B 3/36* | (2006.01) |
| *B01J 10/00* | (2006.01) |
| *B01D 1/14* | (2006.01) |
| *B01B 1/00* | (2006.01) |
| *B01D 1/16* | (2006.01) |
| *C07C 29/141* | (2006.01) |
| *B01J 4/00* | (2006.01) |
| *B01J 19/24* | (2006.01) |

(52) U.S. Cl.
CPC ....... *C07C 45/505* (2013.01); *C01B 2203/1247* (2013.01); *C07C 45/50* (2013.01); *C01B 2203/0255* (2013.01); *B01D 1/14* (2013.01); *C01B 2203/1288* (2013.01); *B01B 1/005* (2013.01); *B01D 1/16* (2013.01); *C07C 29/141* (2013.01); *C01B 2203/1241* (2013.01); *B01J 4/002* (2013.01); *B01J 19/24* (2013.01); *C01B 3/36* (2013.01)
USPC ............ 568/451; 252/373; 422/129; 518/705

(58) Field of Classification Search
USPC ............ 568/451; 252/373; 422/129; 518/705
See application file for complete search history.

(56) References Cited

U.S. PATENT DOCUMENTS

| | | |
|---|---|---|
| 3,980,591 A | 9/1976 | Marion |
| 5,273,212 A | 12/1993 | Gerhardus |
| 5,563,916 A | 10/1996 | Scarpa |

FOREIGN PATENT DOCUMENTS

| | | |
|---|---|---|
| EP | 2103567 A1 | 9/2009 |
| GB | 1568342 | 5/1980 |
| WO | 2009065559 A1 | 5/2009 |

OTHER PUBLICATIONS

International Preliminary Report on Patentability, Jul. 23, 2013.

*Primary Examiner* — Sikarl Witherspoon
(74) *Attorney, Agent, or Firm* — Michael W. Ferrell

(57) ABSTRACT

An improved OXO process with converted waste oil recycle includes: (a) hydroformylating an olefin with synthesis gas in a reactor to produce an OXO product as well as by-product waste oil, the by-product waste oil having a lower or higher boiling temperature than said OXO product; (b) separating OXO product from the by-product waste oil; (c) converting separated waste oil to synthesis gas; and (d) recycling the synthesis gas produced in step (c) to the reactor of step (a).

21 Claims, 4 Drawing Sheets

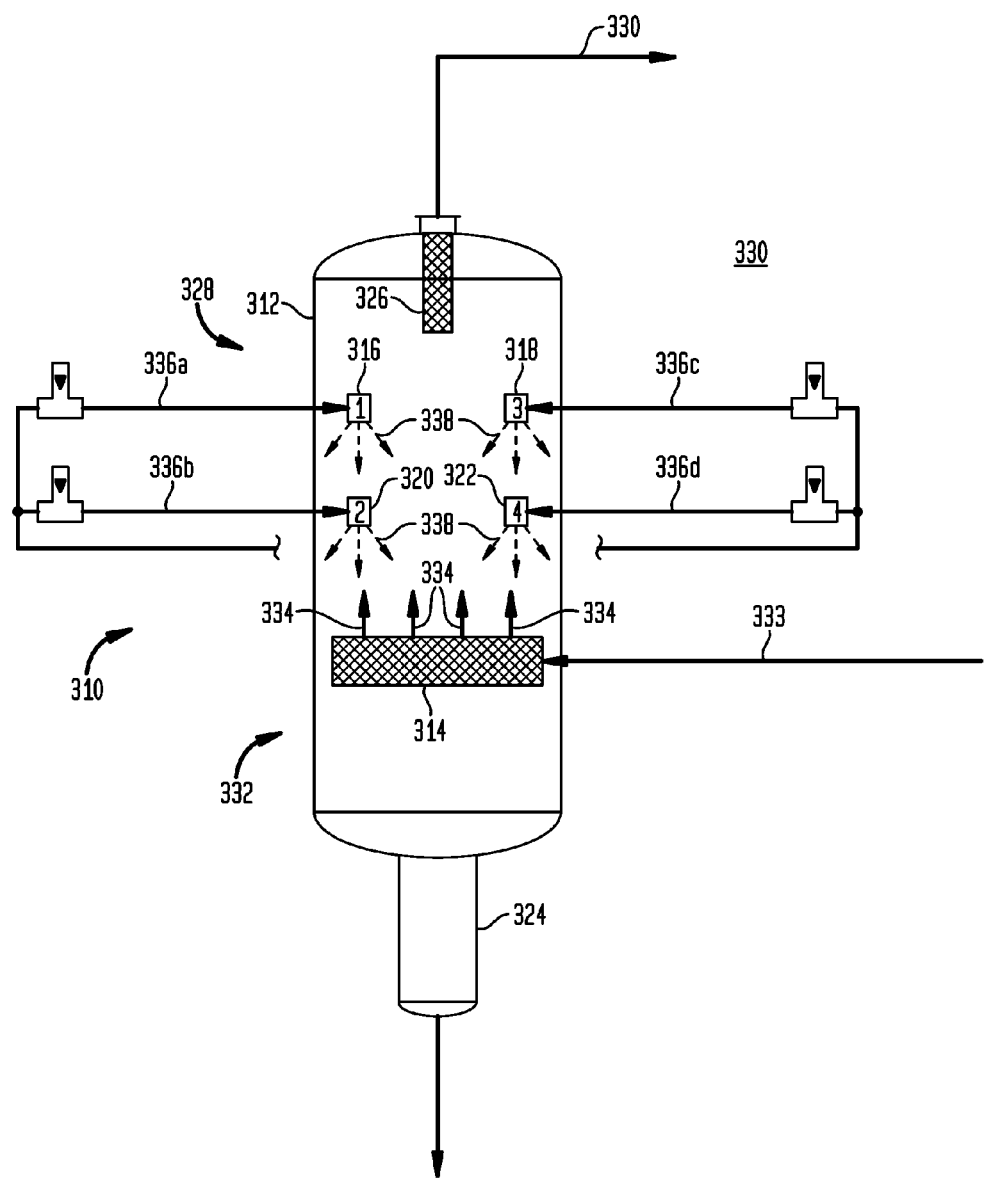

OXO PROCESS AND METHOD FOR PRODUCING SYNTHESIS GAS FROM WASTE OIL

CLAIM FOR PRIORITY

This application is a National Phase application based on application No. PCT/US2012/041471 filed 8 Jun. 2012. This application is also based on U.S. Provisional Patent Application Ser. No. 61/574,259 of the same title, filed Jul. 29, 2011. The priority of of the foregoing applications is hereby claimed and their disclosures are incorporated herein by reference.

FIELD OF THE INVENTION

This invention relates to an improved hydroformylation or OXO process for making aldehydes (and derivatives) from olefin compounds which includes the production of synthesis gas from recycled waste oil recovered as light and heavy by-products in the process. The synthesis gas from the recovered oil is used as a feedstock to the reactor and has a reduced $H_2/CO$ ratio as compared with synthesis gas made from natural gas alone. The inventive method and apparatus may also be used to process other liquid hydrocarbons and/or hydrocarbon oxygenates into synthesis gas.

BACKGROUND OF THE INVENTION

Hydroformylation is a commercially important technology in the chemical industry. Aldehydes are prepared via the hydroformylation or OXO reaction, according to which one mol of unsaturated compound is reacted with synthesis gas (syngas) having a molar ratio of hydrogen to carbon monoxide of 1:1 as shown below:

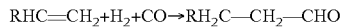

$$RHC=CH_2+H_2+CO \rightarrow RH_2C-CH_2-CHO$$

wherein R is an organic radical. Because of the high chemical reactivity of aldehydes, further chemical derivatives such as alcohols, carboxylic acids, etc. can readily be prepared in large volumes which, in turn, can be further converted into, for example, ester compounds.

Using synthesis gas as the raw material for the OXO reaction requires the adjustment of the molar ratio of the hydrogen to carbon monoxide to levels near 1:1 in many processes and excess of hydrogen has to be removed. In some cases, hydrogen can be used downstream in hydrogenation processes, such as in the manufacture of alcohols or it can be sent to a logistic system for use by further consumers. However, there is a need to decrease the hydrogen to carbon monoxide ratio in order to reduce and/or eliminate excess hydrogen because of the operating and capital expense of removal and redirecting these by-product streams.

The inventive method and apparatus may also be used to process hydrocarbon and other byproduct streams not related to the OXO process, that is oils, alcohols, olefins and other liquids having from 3 to 15 carbon atoms.

In general the liquid waste oils from OXO processes comprise olefinically unsaturated hydrocarbons, longer chain hydrocarbons and oxygenated hydrocarbons. Currently, these liquid waste oils, which generally do not contain any phosphine ($PR_3$) and/or sulfur, are sent to boilers to be incinerated and attempts are made to recover the heat value of these liquid waste oil streams. Heat recovery, while somewhat beneficial, wastes the raw material potential of the oils and requires boiler capacity which is expensive and better utilized on less useful by-products in a chemical plant. Thus, there is a need to more effectively utilize liquid waste oils from an OXO process as well.

Recovered byproduct material may contain a significant amount of non-volatile components which should be removed prior to recycling the material into the production system since these components can cause excessive wear or produce deposits requiring shut-down and cleaning.

In the prior art, the above described deficiencies have not been addressed, despite the availability of numerous technologies to make synthesis gas.

U.S. Pat. No. 3,980,591 discloses a process for recovering particulate carbon using an extractant derived from oxo byproducts, forming a dispersion and using the dispersion as synthesis gas feed.

British Patent Specification 1 568 342 discloses an apparatus for the manufacture of synthesis gas in which a liquid fuel oil and natural gas are mixed and then fed to a vaporizer with a controlled outlet temperature to provide a certain proportion of vapor and liquid. This mixture is then sent to a separator, in which impurities present in the liquid fuel oil are removed as a bottom fraction while a purified vapor fraction goes to the reformer section (page 4, left/right column, bridging lines 48-80, FIG. 1).

WO 2009/065559 discloses a process for producing synthesis gas and hydrogen from liquid hydrocarbon feed stocks generated during refining processes. The recovered hydrocarbon stream is mixed with an oxidizing stream and optionally with a gaseous hydrocarbon stream and then sent to an oxidizing zone wherein a catalytic partial oxidation occurs. Likewise, WO 2009/008092 discloses a process for the production of synthesis gas in the process of the manufacturing of kerosene and gas from natural gas, wherein light hydrocarbons separated by distillation are recycled and treated with steam to produce synthesis gas.

EP 2 103 567 A1 refers to the production of synthesis gas with steam from oxygenated hydrocarbons like glycerol together with natural gas. In this reference, there is described a first step wherein a vapor phase mixture comprising steam and an oxygenated hydrocarbon with a molar ratio of $H_2O:C$ of at least 2 is prepared. Preferably, said mixture is further mixed with natural gas prior to its catalytic conversion into synthesis gas. Further, the oxygenated hydrocarbon is present as droplets of a certain size. The droplets are generated with an atomizing nozzle, which is aided by steam. Generally speaking, introduction of steam increases the hydrogen content of the syngas produced which is undesirable in an OXO process where reduced levels of hydrogen are typically required. Excess hydrogen needs to be removed which adds expense and complexity to the OXO production process as will become apparent from the discussion which follows.

Other references of interest are U.S. Pat. Nos. 7,670,586 and 7,214,720 which include description of synthesis gas preparation.

SUMMARY OF THE INVENTION

An improved OXO process with converted waste oil recycle includes: (a) hydroformylating an olefin with synthesis gas in a reactor to produce an OXO product as well as by-product waste oil, the by-product waste oil having a lower or higher boiling temperature than said OXO product; (b) separating OXO product from the by-product waste oils; (c) converting separated waste oil to synthesis gas comprising evaporating the waste oil with hydrocarbon gas in an evaporator vessel to provide a mixed vapor stream of hydrocarbon gas and evaporated waste oil and directly oxidizing the mixed vapor stream to provide synthesis gas; and (d) recycling the synthesis gas produced in step (c) to the reactor of step (a).

There is provided in other aspects of the invention apparatus and methodology for providing synthesis gas from liquid hydrocarbons or liquid hydrocarbon oxygenates and heated hydrocarbon gas. The liquid hydrocarbon or liquid hydrocarbon oxygenates are evaporated with heated hydrocarbon gas to produce a mixed gaseous stream which is fed to a partial oxidizing unit.

Evaporation of the liquid hydrocarbon/liquid hydrocarbon oxygenates is carried out in an evaporator configured and operated to selectively retain unevaporated liquid in the form of mist or droplets, while the effluent is relatively free of liquid components. Separation of relatively non-volatile components thus occurs in the evaporator which is periodically purged of non-volatile components.

It will be appreciated by one of skill in the art that numerous advantages are realized in connection with the present invention. For one, syngas with a lower $H_2/CO$ ratio relative to natural gas based syngas, reduces hydrocarbon separation costs in connection with an OXO process.

Additional advantages are provided by way of the evaporator design and operation, including that a partial oxidation unit for generating syngas is operated with substantially vaporized feed; for example, vaporized $C_5$-$C_{20}$ liquid hydrocarbons or $C_3$-$C_{20}$ oxygenates including alcohols, aldehydes, ketones, carboxylates and so forth. Because the feed is substantially vaporized, a partial oxidation unit adapted for natural gas feed can be fed higher molecular weight materials with a minimum of modification for introducing the alternate feed. While sooting is typically a problem with liquid-fed syngas oxidation units, low soot operation is readily achieved with the invention because the liquid waste oils are already vaporized and heated. A partial oxidation unit fed with vaporized feed in accordance with the invention can be operated at higher throughputs as compared with a unit with the same feed in liquid form since the liquid feed needs to be vaporized to form syngas, whereas the invention process provides feed in vapor form to the partial oxidation unit.

Low superficial velocity in the evaporator provides separation of non-volatile components in that operation is controlled such that liquid droplets are selectively retained in the evaporator and not entrained from the evaporator to the partial oxidation unit to any great extent. That is, the low superficial velocity is preferably kept below a level that will entrain droplets according to Stokes' law. Generally, the evaporator unit is operated at an upward superficial velocity of less than about 3 ft/sec (0.91 m/sec) and in one especially preferred embodiment, the evaporator is operated at a superficial velocity of 0.5 ft/sec (0.15 m/sec) or less. Heavier and/or non-volatile components that will not vaporize are thus separated from the feed to the partial oxidation unit in the evaporator and may be removed from the system. Contaminants such as residual catalyst, tars and so forth in recycle material thus removed will not foul the syngas reactor or downstream components of a processing system.

Still further aspects and advantages of the invention are discussed below.

DESCRIPTION OF THE DRAWINGS

The invention is described in detail below with reference to the various Figures, wherein like numerals designate similar parts and wherein:

FIG. 4 is a schematic diagram of various features of an evaporator useful in connection with the present invention.

DETAILED DESCRIPTION

Figure 1:
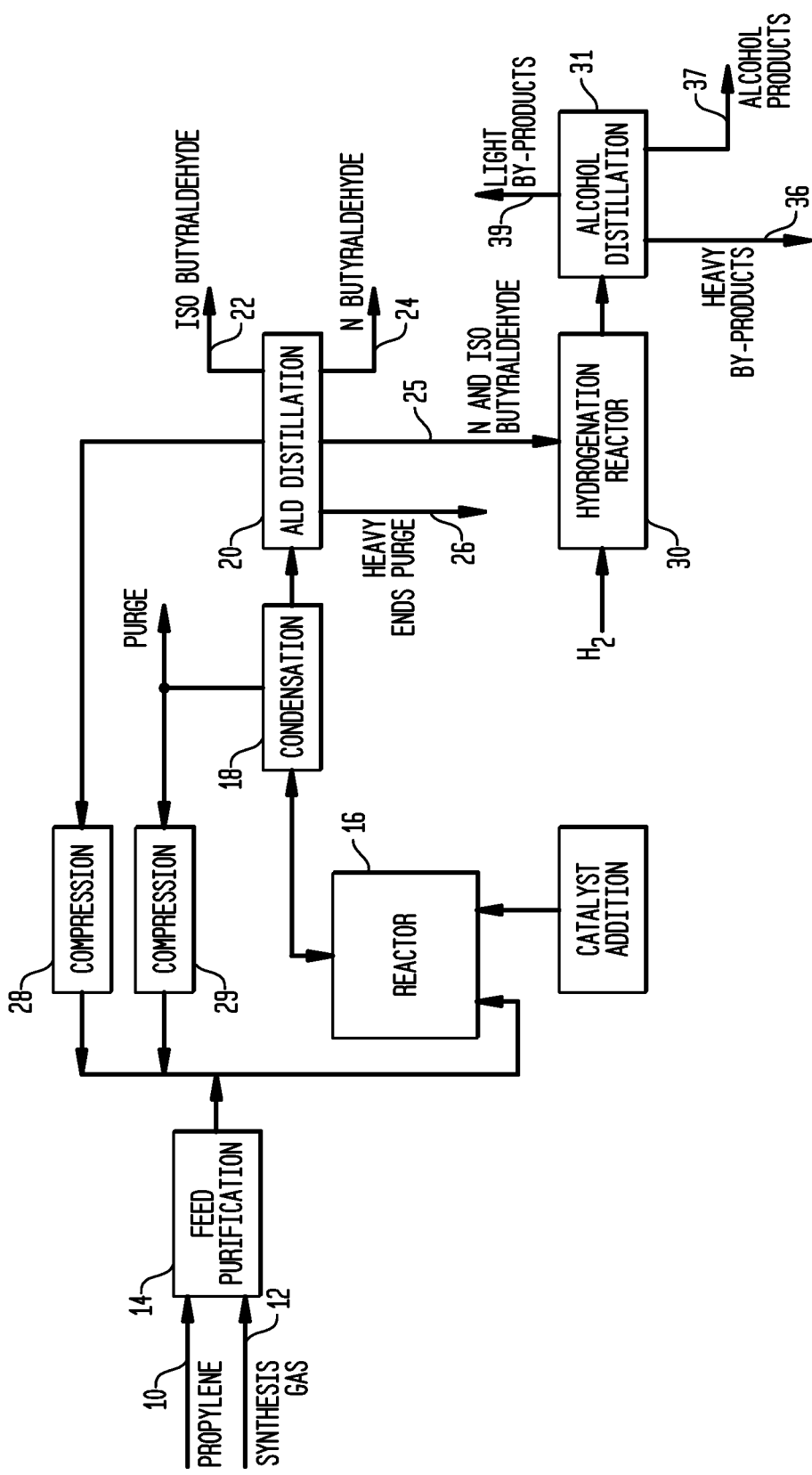
FIG. 1 is a schematic diagram of an OXO process and alcohols unit.

The invention is described in detail below with reference to several embodiments and numerous examples. Such discussion is for purposes of illustration only. Modifications to examples within the spirit and scope of the present invention, set forth in the appended claims, will be readily apparent to one of skill in the art. Terminology used herein is given its ordinary meaning for example, psig refers to gauge pressure in $lbs/inch^2$, standard cubic feet, SCF or like terminology means cubic feet as determined at 60° F. (15.6° C.) and at atmospheric pressure (29.92 inches (760 mm) of mercury absolute) and so forth. Terminology is further defined below.

"Average carbon chain length" refers to the average number of carbons per molecule in a composition based on weight of the components in the mixture.

"Non-catalytic direct partial oxidation" and like terminology refers to the direct reaction of oxygen with a hydrocarbon to produce synthesis gas with or without a moderator gas such as carbon dioxide or steam. Conventionally, a stream of heated natural gas and a separate stream of oxygen are fed into a concentric tube feed injector in a reaction vessel. The feed injector directs the oxygen through a center nozzle surrounding the oxygen in such a way that the streams mix as they leave the feed injector. The partial oxidation (POX) is preferably conducted in the absence of a catalyst.

"Liquid waste oils" and like terminology as used herein generally refers to olefinically unsaturated hydrocarbons, longer chain hydrocarbons and oxygenated hydrocarbons, including alcohols, aldehydes and the like, typically having a two-carbon (C2) to thirty-carbon (C30) molecular structure. A liquid waste oil may be recovered at various locations in an OXO process as hereinafter described. Liquid waste oils are typically liquid under ambient conditions and are liquid as fed to the evaporator.

A liquid hydrocarbon or liquid hydrocarbon oxygenate generally has the attributes of a liquid waste oil, but may be provided from any suitable source. A "liquid hydrocarbon or liquid hydrocarbon oxygenate" thus generally refers to olefinically unsaturated hydrocarbons, longer chain hydrocarbons and oxygenated hydrocarbons, including alcohols, aldehydes and the like, typically having a two-carbon (C2) to thirty-carbon (C30) molecular structure. The present invention is especially suitable for processing higher molecular weight hydrocarbons and hydrocarbon oxygenates having an average carbon chain length of eight-carbons (C8) to thirty-carbons (C30).

"Gaseous hydrocarbon" and like terminology refers to hydrocarbons which are gaseous under ambient conditions and under conditions as fed to the evaporator. Such hydrocarbons may be mixtures such as natural gas or refinery gas and include methane, propane, butane, butylene, ethane, ethylene, pentane, mixtures thereof and so forth. Natural gas, which consists predominantly of methane is preferred. Natural gas may have the typical compositions I or II set forth in U.S. Pat. No. 5,653,916, the disclosure of which is incorporated herein by reference:

Natural Gas with Typical Composition I

| | |
|---|---|
| $CH_4$: | 94.4% by volume |
| $C_2H_6$: | 3.0% |
| $C_3H_8$: | 0.5% |
| $C_4H_{10}$: | 0.2% |
| $C_5H_{10}$: | 0.2% |
| $CO_2$: | 0.2% |
| $N_2$: | 1.5% |

Natural Gas with Typical Composition II

| | |
|---|---|
| $CH_4$: | 81.8% by volume |
| $C_2H_6$: | 2.7% |
| $C_3H_8$: | 0.4% |
| $C_4H_{10}$: | 0.1% |
| $C_5H_{12}$: | 0.1% |
| $CO_2$: | 0.9% |
| $N_2$: | 14.0% |

"OXO" processes are those involving hydroformylation of an olefin as described herein. "OXO products" and like terminology includes products made by hydroformylating olefins and derivatives thereof such as alcohols, acids, esters and so forth.

"Superficial velocity" of gas in the evaporator refers to the volumetric flow rate of gas in the evaporator divided by the cross sectional area of the evaporator through which flow occurs.

This invention then relates, in part, to the preparation of synthesis gas with an enhanced molar ratio of carbon monoxide to hydrogen ratio and the effective use of waste oils generated in other downstream operations. The separated waste oils from the OXO processes and the downstream processes, can be evaporated into a stream of heated natural gas forming a mixture of natural gas and said liquid waste oil which are collectively sent to a partial oxidation unit. Oxygen is provided added via a center nozzle and the mixture of natural gas and evaporated waste oil is added via an annular nozzle surrounding the oxygen, similar to a conventional operation, but without added equipment and/or capital investment.

In one embodiment of the present invention, the liquid waste oils are introduced into a stream of heated natural gas in a vertical evaporation vessel. The vessel can be further equipped with a spray nozzle, packing, and/or trays or any combination thereof in order to enhance the contact time between the liquid waste oils and the gas phases. The contact time is any suitable time which permits evaporation of the waste oil into the natural gas. This contact time can be as little as one second to as high as several minutes depending upon the size of the vessel and the type of contact means provided therein. In another aspect, the liquid waste oils are atomized into a heated stream of natural gas into a countercurrent flow evaporator. Any remaining liquid, which does not evaporate, will be removed from the bottom of the reaction vessel and optionally either recycled into the vessel or otherwise disposed of.

During the hydroformylation reaction of olefins into aldehydes and in the downstream processes of converting said aldehydes into carboxylic acids, alcohols, and esters, both shorter and longer chain hydrocarbons and oxygenated hydrocarbons are separated as light and heavy by-products including liquid waste oils from the desired aldehyde and alcohol products. A somewhat typical OXO process for making butyraldehdye and alcohols is shown schematically in FIG. 1. A stream of propylene 10 and a stream of synthesis gas 12 is fed to a purification system 14 where impurities are removed, hydrogen/carbon monoxide ratios are adjusted and the reactants are forwarded to a reactor 16 which may contain a triphenylphosphine-modified rhodium carbonyl catalyst. In the reactor butyraldehyde and by-products are produced and forwarded to a condensation section 18 before being sent to a distillation section 20, and on to hydrogenation section 30. In section 20, the products are separated as streams 22, 24 and 25 from heavy by-products which exit in a stream 26. Stream 26 contains liquid waste oils typically having six-carbon (C6) to fourteen carbon (C14) chains and longer for higher molecular weight products. In a continuous process, gasses are recycled via compressors 28, 29 as shown in FIG. 1. Stream 25 is further processed through a hydrogenation reactor 30 with the addition of hydrogen. Alcohol products 37 are separated from light by-products 39 and heavy by-products 36 in a distillation section 31. Stream 39 contains liquid waste oils typically having four-carbons (C4) or less for lower molecular weight products.

In general the liquid waste oils from streams 26, 36, and 39 comprise olefinically unsaturated hydrocarbons, longer chain hydrocarbons and oxygenated hydrocarbons.

Referring to FIG. 1, there is shown an OXO process for producing butyraldehyde in linear and branched form from propylene. One of skill-in-the-art will appreciate that other materials may be used in an OXO process. Principal commercial olefin feedstocks include linear and branched $C_2$-$C_{17}$ monoolefins. Among the primarily linear type are ethylene, propylene, and 1- and 2-butenes; α-olefin mixtures of varying chain length derived from growth reaction of ethylene on aluminum alkyls or from wax cracking; and mixtures of predominantly internal olefins from dehydrogenation or chlorination-dehydrochlorination of η-paraffins or from ethylene oligomerization. Branched-chain olefins include amylenes from petroleum cracking; heptenes, octenes, nonenes, and dodecenes from fractionation of oligomers of $C_3$-$C_4$ olefins; and octenes from dimerization and codimerization of isobutylene and 1- and 2-butenes. Linear terminal olefins are the most reactive reagents in conventional cobalt-hydroformylation; linear internal olefins react less than one third as fast. A single methyl branch at the olefinic carbon of a terminal olefin reduces its reaction rate by a factor of ten, but the effect of a branch diminishes as its distance from the double bond increases. Some C6 feedstocks which exhibit different reactivities include: 1-hexene; 4-methyl-1-pentene; 2-hexene; 4-methyl-2-pentene; 2-methyl-1-pentene; 2-methyl-2-pentene; and 2,3-dimethyl-2-butene.

Figure 2:
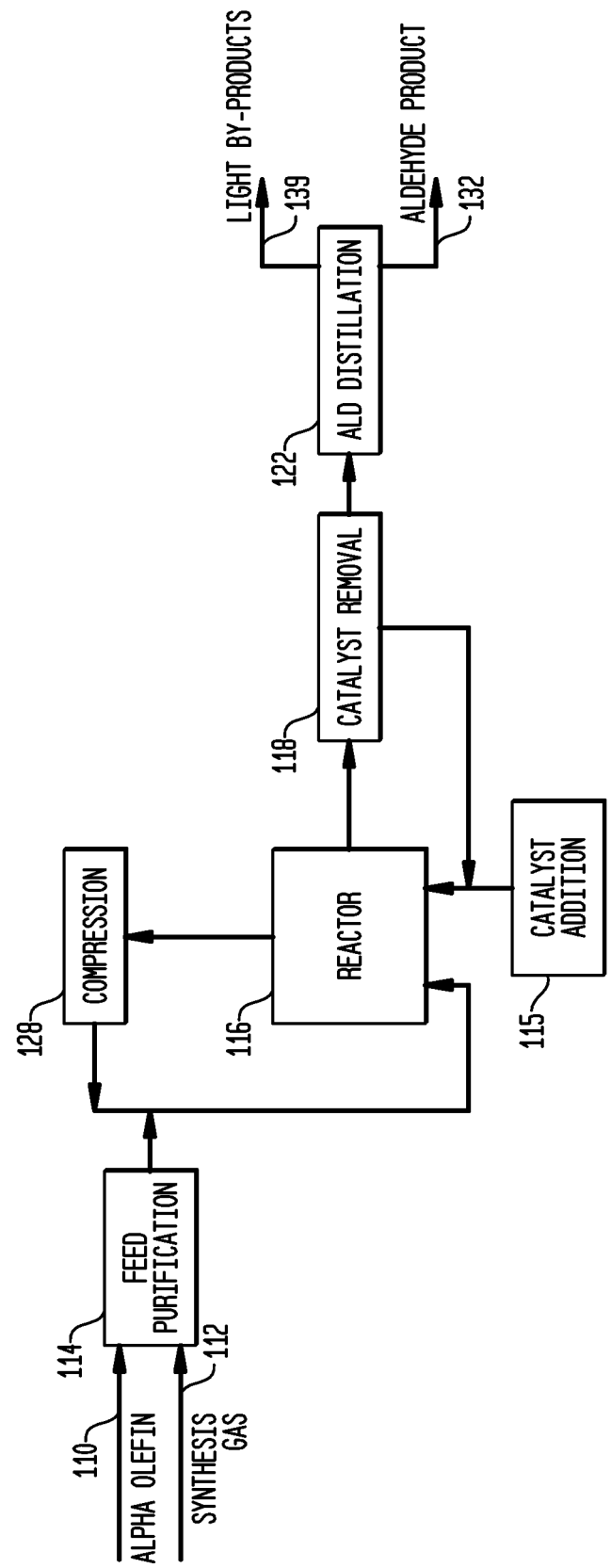
FIG. 2 is a schematic diagram of another OXO process.

There is shown in FIG. 2 an alternate OXO process which may be utilized in connection with the present invention. The process illustrated in FIG. 2 is especially suitable for longer chain olefins. In connection with the OXO process of FIG. 2, α-olefin feedstock is fed via line 110 and synthesis gas is provided via line 112. Both the α-olefin and the syngas are purified at 114 and the hydrogen/CO ratio is adjusted via membrane separation or otherwise to achieve the desired mix. After purification, the reactants are provided to reactor 116 for hydroformylation. The reactor is coupled to a catalyst reservoir 115 and unreacted reactants are compressed and recycled at 128 as shown. After reaction, catalyst is removed from the crude product at 118 and recycled to the system. The aldehyde product is distilled at 122 and crude product exits at 132 while light by-products are recovered at 139.

Further details concerning various OXO processes are set forth in *Kirk-Othmer Encyclopedia of Chemical Technology*, $3^{rd}$. Ed., Vol. 11, pp. 637-653 (Wiley, 1980), the disclosure of which is incorporated herein by reference.

Figure 3:
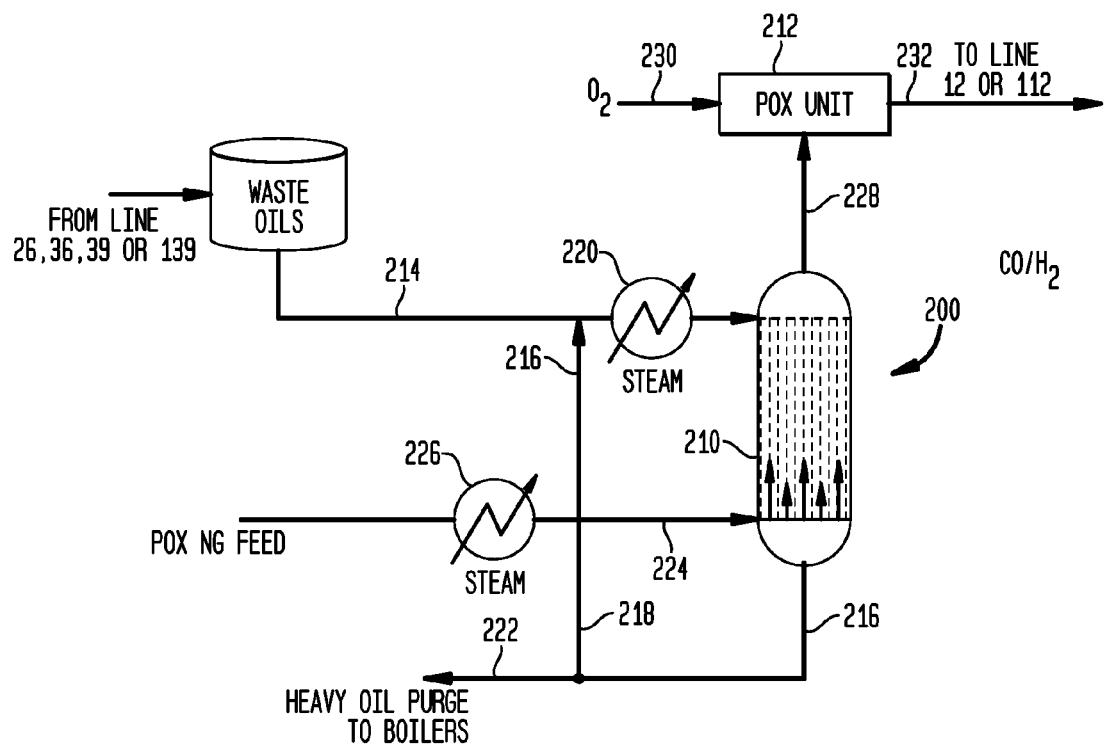
FIG. 3 is a schematic diagram of an apparatus for producing synthesis gas in connection with the apparatus of FIG. 1 or the apparatus of FIG. 2 using a mixture of natural gas and waste oils.

In accordance with the invention there is provided an apparatus 200 shown in FIG. 3 for use in connection with the OXO processes in FIGS. 1 and 2. Apparatus 200 includes an evaporator vessel 210 and a partial oxidation (POX) unit 212. Evaporator 210 is fed waste oils from the OXO unit of FIG. 1, for example, derived from line 26, 36, and/or 39 or from line 139 of FIG. 2 and forwarded to waste oil feed line 214. The waste oil is fed to the recycle system 216 which includes piping 218 and steam heat exchanger 220. Oil may be periodically purged from system 216 via line 222. Natural gas is fed to evaporator vessel 210 through line 224 which preferably is a heated line communicating with another stream heat exchanger 226.

Evaporator vessel 210 has an output of the evaporator unit 228 which connects with partial oxidation unit 212 which is fed oxygen and optionally a moderator gas such as $CO_2$ or steam via line 230. Unit 212 is of a conventional non-catalytic direct oxidation type with an annular burner. Details as to materials and construction generally are provided in U.S. Pat. No. 5,563,916 to Disselhorst et al., as well as U.S. Pat. No. 5,273,212 to Gerhardus et al., the disclosures of which are incorporated herein by reference. The partial oxidation unit is optionally provided with a membrane system (not shown) to provide a 1:1 molar ratio mixture of hydrogen and carbon monoxide as syngas output as is well known in the art.

In operation, apparatus 200 is fed liquid waste oil via line 214, to piping 216 to an upper portion of evaporator 210 where the oil is atomized and directed generally downwardly through a fixed or movable set of nozzles while heated natural gas is fed to vessel 210 via line 224 at elevated temperatures. The heated natural gas is discharged generally in a direction of flow upwardly as shown; that is, counter-current to the atomized liquid waste oil which flows downwardly. A mixed feed stream of natural gas and evaporated waste oil is provided to POX unit 212 which is also provided oxygen via line 230 to oxidize the mixed vapor feed stream to produce synthesis gas which exits the POX unit via line 232 and is provided to an OXO process, for example, line 12 of the butyraldehyde process shown in FIG. 1 or line 112 of the process illustrated in FIG. 2.

There is shown schematically in FIG. 4 another diagram of various features of an evaporator 310 which may be utilized in connection with the processes and apparati shown in FIGS. 1-3. Evaporator 310 includes a vessel 312 provided with a gas distributor 314 as well as a plurality of nozzle assemblies 316, 318, 320 and 322. At the base of the vessel 312 is a liquid catch-basin 324, while a mist eliminator 326 is provided at an upper portion 328 of vessel 312 around exit line 330. Gas distributor 314 is disposed at a lower portion 332 of vessel 312.

Four nozzle assemblies 316, 318, 320 and 322 are located at upper portion 328 of vessel 312 at a common level and are spaced equally at 90° or so around the vessel.

In operation, heated gas is fed to the vessel via line 333 and exits upwardly from the gas distributor as shown by arrows 334, while liquid oil is fed to nozzle assemblies 316-322 via lines 336a-d as shown and sprayed downwardly as indicated by arrows 338 inside of the vessel. Superficial velocity in vessel 312 is kept low, preferably below 0.5 ft/sec (0.15 m/sec) so that oil droplets are not entrained upwardly (Stokes' law) through effluent line 330 which is coupled to a partial oxidation (POX) unit to make syngas. The heated gas vaporizes the liquid hydrocarbons or liquid hydrocarbon oxygenates in the evaporator and the mixed gaseous stream is optionally passed through a mist eliminator such as eliminator 326 prior to exiting the evaporator. Stream 330 is thus substantially in gaseous form (free of liquid oils). Unevaporated liquid accumulates in catch-basin 324 and may be recycled through the nozzles and periodically purged from the system to remove impurities Further features and details of the apparatus are discussed below.

Referring to FIG. 4, the evaporator vessel is generally cylindrical in shape and is approximately 5 to 50 feet (1.5 to 15 m) in height and 2 to 15 feet (0.6 to 4.6 m) in diameter. The materials of construction of this vessel are commonly known for this type of reaction process. The natural gas is heated by a steam unit and then fed into the evaporator vessel. The natural gas is under pressures of anywhere from about 50 psig (0.345 MPa/g) to about 1000 psig (6.9 MPa/g), and at flow rates of from about 300 (8.5 $m^3$) to about 1000 (28.3 $m^3$) standard cubic feet per minute. The heated natural gas is injected into the interior of vessel through concentric pipes/rings (not shown) through upwardly directed openings. The liquid waste oils are injected into the evaporator vessel into the upper portion thereof, preferably in such a manner so that they are atomized and flow downwardly countercurrent to the natural gas. Thus, there is a countercurrent flow of materials, that is, the liquid waste oils are traveling in a downward manner and the gas) flowing in an upward manner. The liquid waste oils are flowing/pumped at a rate of approximately 2 (7.6 l) to 10 (27.9 l) gallons per minute and at pressures of about 500 psig (3.45 MPa/g) to 1500 psig (10.34 MPa/g). Where necessary, the liquid waste oils can be steam heated in a manner like that shown in FIG. 3. Under some circumstances, one or more filters may be used to remove any undesired solid materials. An interior pipe (not shown) for feeding the waste oils can be fixed or so constructed as to be moved upward and/or downward depending upon the reaction conditions and material flow rates contained therein and also to provide the greatest flexibility in contact time between the liquid and gas phases. The interior pipe can be a circular pipe having holes therein and spraying the liquid oils in a downward fashion similar to a modern spray dryer. Likewise, the evaporator can be configured with trays, random or structured packing, or other similar devices in order to facilitate suitable contact between the liquid and gas phases flowing in a counter-current manner. In general, it is desirable to maintain the temperature within the evaporator vessel at about 350° F. (177° C.) to about 500° F. (260° C.) and at a pressure range of about 700 (4.83 MPa/g) psig to about 1500 (10.34 MPa/g) psig.

As previously mentioned, one of the unique features of the present invention relates to the increase in the molar content of the carbon monoxide in the synthesis. This increase is generally in the range of from about 1 percent to about 6 percent. The other unique feature is the more effective use of the liquid waste oils and the decrease in the downstream boiler load and which in turn results in the utilization of the boiler for other material processing. Furthermore, this invention does not require a catalyst for the production of the synthesis gas with enhanced carbon monoxide content.

In a specific construction, the evaporator vessel has a diameter of 4 feet (1.2 m) and a height of 8 feet (2.4 m). The vessel is provided with appropriate heating/cooling means to maintain an interior temperature within the range 350° F. (177° C.) to 450° F. (232° C.). The waste liquid oils are fed into the upper portion on the vessel at a position of approximately 4 feet (1.2 m) from the top thereof. The interior section of the liquid oil feed is configured in the form of a circular pipe having perforations therein and attached thereto are nozzles so as to atomize the oils into droplets sprayed in a downward direction. The oils are supplied to the interior of the vessel at a flow rate of 5 gallons (18.9 l) per minute and at a pressure of about 1000 psig (6.9 MPa/g). The natural gas is supplied to the interior of the vessel at a point approximately 4 feet (1.2 m) from the bottom most portion of the vessel. The natural gas is preheated to a temperature range of from about 400° F. (204° C.) to about 1000° F. (538° C.) by an indirect heat exchanger, and then each preheated natural gas is supplied at a flow rate of approximately 600 cubic feet (17 m$^3$) per minute.

The synthesis gas leaving the upper most portion of the POX unit is periodically sampled and analyzed for carbon monoxide content and it is found that the carbon oxide content has increased on the average of from about 4.6 to about 5.1 mole percent, and is compared with the same unit operated without the utilization of the liquid waste oils.

To further demonstrate utility and advantages in connection with syngas production, the apparatus shown in FIGS. 3 and 4 was operated with increasing levels of waste oil over a period of about 2.3 hours fed via line 214 at constant natural gas flow as shown in Table 1, below. 1:1, CO:H$_2$ molar ratio output (regulated by membrane in production) via line 232 increased as waste oil feed increased as is demonstrated in the table.

TABLE 1

1:1 Syngas Production With Increasing Oil Feed

| Oil Feed Units/Min | 1:1 Syngas Output as % of Starting Flow |
|---|---|
| 0 | 100.0% |
| 2.39 | 100.1% |
| 3.916 | 100.0% |
| 4.025 | 100.0% |
| 4.014 | 100.2% |
| 4.634 | 100.9% |
| 4.9 | 101.6% |
| 4.934 | 102.8% |
| 4.989 | 103.3% |
| 5.015 | 103.8% |
| 5.003 | 103.9% |
| 4.979 | 103.8% |
| 4.997 | 103.9% |
| 5.003 | 104.2% |
| 5.018 | 104.4% |

It will be appreciated from the data in Table 1 that the waste oil feed significantly de-bottlenecks production of 1:1 syngas while recovering chemical feedstock value from the waste oil which would otherwise be incinerated or disposed of as waste. The inventive system thus improves raw material usage as well as reduces waste.

It will be appreciated from the foregoing that the invention provides the following features: (a) the evaporator vessel is provided with means to increase the contact time between the waste oils, natural gas; (b) natural gas is injected into the evaporator at a flow rate of about 500 (14.2 m$^3$) to 1000 cubic feet (28.4 m$^3$) per minute and at a pressure from about 50 (0.345 MPa/g) to 1000 psig (6.9 MPa/g); (c) the evaporator is provided with means to maintain the temperature therein at about 250° F. (121° C.) to about 750° F. (399° C.); (d) the evaporator is substantially cylindrical in shape and has a diameter of 2 to about 15 feet (0.61 to 4.6 m) and a height of about 5 (1.5 m) to about 50 feet (15 m); and (e) the waste oil syngas process of the invention produces from 1% to about 6% mole percent more carbon monoxide as compared to the same process which does not use waste oils.

Generally, there is thus provided in accordance with the invention an improved OXO process with converted waste oil recycle comprising: (a) hydroformylating an olefin with synthesis gas in a reactor to produce an OXO product as well as by-product waste oil, the by-product waste oil having a lower or higher boiling temperature than said OXO product; (b) separating OXO product from the by-product waste oil; (c) converting separated waste oil to synthesis gas comprising evaporating the waste oil with hydrocarbon gas in an evaporator vessel to provide a mixed vapor stream of hydrocarbon gas and evaporated waste oil and directly oxidizing the mixed vapor stream to provide synthesis gas; and (d) recycling the synthesis gas produced in step (c) to the reactor of step (a). The step of converting the waste oil to synthesis gas preferably includes evaporating the waste oil with hydrocarbon gas in an evaporator vessel to provide a mixed vapor stream of hydrocarbon gas and evaporated waste oil and directly oxidizing the mixed vapor stream to provide synthesis gas. Typically, the hydrocarbon gas is natural gas and the temperature in the evaporator vessel is maintained between 250° F. (121° C.) and 750° F. (399° C.). Suitably, the temperature in the evaporator vessel is maintained between 350° F. (177° C.) and 500° F. (260° C.) and the pressure in the evaporator vessel is maintained between 500 psig (3.45 MPa/g) and 1500 psig (10.34 MPa/g) while waste oil is injected into the evaporator vessel under a pressure of above 500 psig (3.45 MPa/g) up to about 1500 psig (10.34 MPa/g).

The synthesis gas produced generally has a molar ratio of H$_2$/CO of from 1.65 to 1.85; typically the synthesis gas produced has a molar ratio of H$_2$/CO of from 1.7 to 1.75.

In many cases the olefin supplied to the reactor comprises a two carbon (C2) to seventeen carbon (C17) mono olefin so that the OXO product comprises a three carbon (C3) to eighteen carbon (C18) aldehyde or a three carbon (C3) to eighteen carbon (C18) alcohol. Preferred products include propionaldehyde or butyraldehyde.

In another aspect of the invention there is provided a method of making synthesis gas from a hydrocarbon gas and a hydrocarbon liquid and/or hydrocarbon oxygenate liquid including the steps of: (a) feeding hydrocarbon gas at elevated temperature to an evaporator vessel; (b) concurrently with step (a), feeding a hydrocarbon liquid and/or hydrocarbon oxygenate liquid to the evaporator vessel through one or more nozzle assemblies to provide atomized liquid to the evaporator; (c) wherein at least 30 standard cubic feet (0.85 m$^3$) of hydrocarbon gas is provided to the evaporator per gallon (3.7853 l) of liquid feed; (d) evaporating the liquid with the hydrocarbon gas to provide a mixed feed stream of hydrocarbon gas and vaporized liquid to a partial oxidation unit; and (e) oxidizing the mixed feed stream by contacting the mixed feed stream with oxygen in the partial oxidation unit to produce synthesis gas. The liquid feed to the evaporator generally includes hydrocarbon liquid and/or hydrocarbon oxygenate liquid with an average carbon chain length of from two carbons (C2) to thirty carbons (C30); typically the liquid feed to the evaporator comprises hydrocarbon liquid and/or hydrocarbon oxygenate liquid with an average carbon chain length of from six carbons (C6) to thirty carbons (C30). In some cases the liquid feed to the evaporator comprises hydrocarbon liquid and/or hydrocarbon oxygenate liquid with an average carbon chain length of from ten carbons (C10) to thirty carbons (C30). In one preferred embodiment, the liquid feed to the evaporator is waste oil is from an OXO aldehyde process, or OXO alcohol process, and the synthesis gas produced has a molar ratio of H$_2$/CO of more than 1.65 and less than 1.85. More typically, the synthesis gas produced may have a molar ratio of H$_2$/CO of more than 1.7 and less than 1.75.

In preferred embodiments, oxidizing the mixed feed stream is by way of direct oxidation without a catalyst.

To provide for complete vaporization it may be desirable to provide at least 50 standard cubic feet (1.42 m$^3$) of hydrocarbon gas is provided to the evaporator per gallon (3.7853 l) of liquid feed; although anywhere from 30 standard cubic feet (0.85 m$^3$) to 500 standard cubic feet (14.16 m$^3$) of hydrocarbon gas may be provided to the evaporator per gallon (3.7853 l) of liquid feed. More typically, from 50 standard cubic feet (1.42 m$^3$) to 200 standard cubic feet (5.66 m$^3$) of hydrocarbon gas is provided per gallon (3.7853 l) of liquid feed, such as from 75 standard cubic feet (2.12 m$^3$) to 150 standard cubic feet (4.25 m$^3$) of hydrocarbon gas per gallon (3.7853 l) of liquid feed.

A preferred hydrocarbon gas to use in the inventive process is natural gas.

In a preferred construction, the evaporator is fed liquid through one or more nozzle assemblies in a downward direction and the hydrocarbon gas is fed upwardly countercurrent to the liquid feed and wherein the mixed feed stream of hydrocarbon gas and vaporized liquid is withdrawn from the evaporator at an upper portion thereof. The upward superficial velocity of the gas in the evaporator is generally less than 3 ft/sec (0.91 m/sec); but may be less than 2 ft/sec (0.61 m/sec), or less than 1.5 ft/sec (0.46 m/sec); even less than 1 ft/sec (0.31 m/sec) or less than 0.5 ft/sec (0.15 m/sec). In most cases the upward superficial velocity of the gas in the evaporator is from 0.1 ft/sec (0.03 m/sec) up to 3 ft/sec (0.91 m/sec).

In still another aspect of the invention, there is provided apparatus for production of synthesis gas comprising: (a) an evaporation unit with a heated hydrocarbon gas feed, a liquid feed for liquid hydrocarbons and/or liquid hydrocarbon oxygenates as well as an evaporator vessel coupled to the gas feed and liquid feed, the evaporator vessel also being coupled to an output of the evaporation unit, wherein the evaporation vessel has an upper portion and a lower portion and includes: (a) one or more nozzle assemblies disposed in its upper portion configured to feed liquid downwardly into the evaporation vessel; (b) a gas distributor disposed in its lower portion configured to feed heated hydrocarbon gas upwardly into the evaporation vessel. A third feature (c) is wherein further the evaporation vessel is coupled to the output of the evaporation unit at the upper portion of the evaporation vessel and is configured and adapted to operate at feed rates, pressures and temperatures to evaporate liquid hydrocarbons and/or liquid hydrocarbon oxygenates and provide a mixed vapor stream of hydrocarbon gas and evaporated liquid hydrocarbon and/or hydrocarbon oxygenate to the output of the evaporation unit while maintaining an upward superficial gas velocity of less than 3 ft/sec (0.91 m/sec) in the evaporation vessel. A partial oxidation unit (d) is coupled to the output of the evaporator unit and adapted to receive the mixed vapor feed of hydrocarbon gas and evaporated liquid from the evaporator unit; the partial oxidation unit is further provided with an oxygen injector which provides oxygen to the mixed vapor feed and converts it to synthesis gas. The evaporator vessel is optionally provided with a liquid recycle system which transports liquid from the lower portion of the evaporator vessel to the upper portion of the evaporator vessel. The the waste oil recycle system may include a heater and a purge.

In one preferred embodiment, the partial oxidation unit is a non-catalytic partial oxidation unit which includes an annular burner for oxidizing mixed vapor feed of hydrocarbon gas and evaporated liquid. Further features which may be included are wherein the evaporator vessel is equipped with at least 2 or perhaps 4 nozzle assembles disposed in its upper portion configured to feed liquid downwardly into the evaporation unit and wherein the evaporator vessel is provided with a mist eliminator. The evaporator is preferably operated at a superficial gas velocity in the evaporator of less than 2 ft/sec (0.61 m/sec) and a ratio of gas/liquid feed of at least 30 standard cubic feet (0.85 m$^3$) of hydrocarbon gas per gallon (3.7853 l) of liquid as noted hereinabove.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

What is claimed is:

1. An improved OXO process with converted waste oil recycle comprising:
    a. hydroformylating an olefin with synthesis gas in a reactor to produce an OXO product as well as by-product waste oil, the by-product waste oil having a lower or higher boiling temperature than said OXO product;
    b. separating OXO product from the by-product waste oil;
    c. converting separated waste oil to synthesis gas comprising evaporating the waste oil with hydrocarbon gas in an evaporator vessel to provide a mixed vapor stream of hydrocarbon gas and evaporated waste oil and directly oxidizing the mixed vapor stream to provide synthesis gas; and
    d. recycling the synthesis gas produced in step (c) to the reactor of step (a).

2. The improved OXO process according to claim 1, wherein the hydrocarbon gas is natural gas.

3. The improved OXO process according to claim 1, wherein the temperature in the evaporator vessel is maintained between 250° F. (121° C.) and 750° F. (399° C.).

4. The improved OXO process according to claim 1, wherein pressure in the evaporator vessel is maintained between 500 psig (3.45 MPa/g) and 1500 psig (10.34 MPa/g).

5. The improved OXO process according to claim 1, wherein the synthesis gas produced has a molar ratio of H$_2$/CO of from 1.65 to 1.85.

6. The improved OXO process according to claim 1, wherein the olefin supplied to the reactor comprises a two carbon (C2) to seventeen carbon (C17) mono olefin.

7. A method of making synthesis gas from a hydrocarbon gas and a hydrocarbon liquid and/or hydrocarbon oxygenate liquid comprising:
    a. feeding hydrocarbon gas at elevated temperature to an evaporator vessel;
    b. concurrently with step (a), feeding a hydrocarbon liquid and/or hydrocarbon oxygenate liquid to the evaporator vessel through one or more nozzle assemblies to provide atomized liquid to the evaporator;
    wherein at least 30 standard cubic feet (0.85 m$^3$) of hydrocarbon gas is provided to the evaporator per gallon (3.7853 l) of liquid feed;
    c. evaporating the liquid with the hydrocarbon gas to provide a mixed feed stream of hydrocarbon gas and vaporized liquid to a partial oxidation unit; and
    d. oxidizing the mixed feed stream by contacting the mixed feed stream with oxygen in the partial oxidation unit to produce synthesis gas.

8. The method according to claim 7, wherein the liquid feed to the evaporator comprises hydrocarbon liquid and/or hydrocarbon oxygenate liquid with an average carbon chain length of from six carbons (C6) to thirty carbons (C30).

9. The method according to claim 7, wherein the liquid feed to the evaporator is waste oil is from an OXO aldehyde process, or OXO alcohol process.

10. The method according to claim 7, wherein oxidizing the mixed feed stream is by way of direct oxidation without a catalyst.

11. The method according to claim 7, wherein from 50 standard cubic feet (1.42 m$^3$) to 200 standard cubic feet (5.66 m$^3$) of hydrocarbon gas is provided per gallon (3.7853 l) of liquid feed.

12. The method according to claim 7, wherein from 75 standard cubic feet (2.12 m$^3$) to 150 standard cubic feet (4.25 m$^3$) of hydrocarbon gas is provided per gallon (3.7853 l) of liquid feed.

13. The method according to claim 7, wherein the evaporator is fed liquid through one or more nozzle assemblies in a downward direction and the hydrocarbon gas is fed upwardly countercurrent to the liquid feed and wherein further the mixed feed stream of hydrocarbon gas and vaporized liquid is withdrawn from the evaporator at an upper portion thereof.

14. The method according to claim 13, wherein the upward superficial velocity of the gas in the evaporator is less than 3 ft/sec (0.91 m/sec).

15. The method according to claim 13, wherein the upward superficial velocity of the gas in the evaporator is less than 1 ft/sec (0.31 m/sec).

16. The method according to claim 13, wherein the upward superficial velocity of the gas in the evaporator is less than 0.5 ft/sec (0.15 m/sec).

17. Apparatus for production of synthesis gas comprising:
   a. an evaporation unit with a heated hydrocarbon gas feed, a liquid feed for liquid hydrocarbons and/or liquid hydrocarbon oxygenates as well as an evaporator vessel coupled to the gas feed and liquid feed, the evaporator vessel also being coupled to an output of the evaporation unit,
   wherein the evaporation vessel has an upper portion and a lower portion and includes:
      (i) one or more nozzle assemblies disposed in its upper portion configured to feed liquid downwardly into the evaporation vessel;
      (ii) a gas distributor disposed in its lower portion configured to feed heated hydrocarbon gas into the evaporation vessel; and
   wherein further the evaporation vessel is coupled to the output of the evaporation unit at the upper portion of the evaporation vessel and is configured and adapted to operate at feed rates, pressures and temperatures to evaporate liquid hydrocarbons and/or liquid hydrocarbon oxygenates and provide a mixed vapor stream of hydrocarbon gas and evaporated liquid hydrocarbon and/or hydrocarbon oxygenate to the output of the evaporation unit while maintaining an upward superficial gas velocity in the evaporation vessel of less than 3 ft/sec (0.91 m/sec) in the evaporation vessel; and
   b. a partial oxidation unit coupled to the output of the evaporator unit adapted to receive the mixed vapor feed of hydrocarbon gas and evaporated liquid from the evaporator unit; the partial oxidation unit being provided with an oxygen injector which provides oxygen to the mixed vapor feed and converts it to synthesis gas.

18. Apparatus according to claim 17, wherein the evaporator vessel is provided with a liquid recycle system which transports liquid from the lower portion of the evaporator vessel to the upper portion of the evaporator vessel.

19. Apparatus according to claim 17, wherein the partial oxidation unit is a non-catalytic partial oxidation unit.

20. Apparatus according to claim 17, wherein the gas distributor is configured to feed gas upwardly into the evaporation vessel.

21. Apparatus according to claim 17, wherein the evaporator vessel is provided with a mist eliminator.

* * * * *